United States Patent [19]
Kilpatrick-Liverman et al.

[11] Patent Number: 5,639,463
[45] Date of Patent: Jun. 17, 1997

[54] CLEAR COSMETIC STICK COMPOSITION

[75] Inventors: LaTonya K. Kilpatrick-Liverman, Princeton, N.J.; Andrea Motyka, Doylestown, Pa.; Bhalchandra D. Moghe, Scotch Plains, N.J.; Radhakrishna B. Kasat, Bellemead, N.J.; Makarand Shevade, Plainsboro, N.J.

[73] Assignee: The Mennen Company, Morristown, N.J.

[21] Appl. No.: 448,101

[22] Filed: May 23, 1995

[51] Int. Cl.⁶ .............................. A61K 6/00; A61K 38/74
[52] U.S. Cl. .................... 424/401; 424/65; 424/78.02; 424/78.08; 424/78.18; 424/400; 512/1; 514/944; 514/946
[58] Field of Search ........................ 424/65, 400, 401, 424/78.02, 78.08, 78.18; 512/1; 514/944, 946

[56] References Cited

U.S. PATENT DOCUMENTS

| | | | |
|---|---|---|---|
| 5,128,123 | 7/1992 | Brewster et al. | 424/65 |
| 5,162,378 | 11/1992 | Guthauser | 514/785 |
| 5,198,218 | 3/1993 | Kuznitz et al. | 424/401 |
| 5,221,529 | 6/1993 | Brazinsky | 424/65 |
| 5,393,526 | 2/1995 | Castro | 424/195.1 |
| 5,424,070 | 6/1995 | Kasat et al. | 424/401 |
| 5,458,880 | 10/1995 | Kasat et al. | 424/401 |
| 5,462,736 | 10/1995 | Rech et al. | 424/401 |
| 5,463,098 | 10/1995 | Giovanniello | 556/27 |

FOREIGN PATENT DOCUMENTS

| | | |
|---|---|---|
| 0089120A2 | 2/1983 | European Pat. Off. . |
| 0251679A2 | 6/1987 | European Pat. Off. . |
| 0450597A2 | 4/1991 | European Pat. Off. . |
| 067619A2 | 2/1995 | European Pat. Off. . |
| WO92/05767 | 4/1992 | WIPO . |
| WO94/27567 | 12/1994 | WIPO . |

*Primary Examiner*—Terressa Mosley
*Attorney, Agent, or Firm*—Antonelli, Terry, Stout & Kraus, LLP

[57] ABSTRACT

The present invention is directed to a clear cosmetic stick composition (e.g., a clear deodorant stick composition) gelled with a soap gelling agent and containing alcohol and water, the composition further containing alkoxylate materials selected from alkoxylate homopolymers and/or dimethicone copolyols as clarifying agents. Illustrative clarifying agents include C14-15 Pareth-2.25, C14-15 Pareth-13, Ceteareth-55, PPG-10 Cetyl Ether, PEG-6 Lauramide, and dimethicone copolyols with ethylene oxide and/or propylene oxide side chains. The stick composition having the clarifying agents of the present invention has improved clarity and maintains clarity for extended periods of time, and has improved pliability while maintaining rigidity of the stick product.

23 Claims, No Drawings

CLEAR COSMETIC STICK COMPOSITION

BACKGROUND OF THE INVENTION

The present invention relates to cosmetic stick compositions, i.e., cosmetic solid stick compositions such as deodorant solid stick compositions. More specifically, the present invention relates to cosmetic solid stick compositions containing an alcohol (for example, a monohydric alcohol, such as ethanol, or a polyhydric alcohol, such as propylene glycol) and water, and gelled with a soap (for example, an alkali metal salt of a saturated fatty acid). In particular, the present invention relates to clear cosmetic solid stick compositions with improved clarity, so as to achieve an improved appearance, which retain such improved clarity over an extended period of time, and which have improved pliability while maintaining satisfactory rigidity.

The present invention is especially related to clear, soap-gelled deodorant stick compositions that are clear and maintain such clarity for extended periods of time, and which have improved pliability while maintaining rigidity, the compositions containing a deodorant active material such as a fragrance and/or an antibacterial agent. However, the present invention is not limited to clear, soap-gelled deodorant stick compositions, but has general applicability to other clear sticks. That is, depending on the cosmetic active ingredient incorporated in the stick composition (for example, a deodorant active ingredient, an insect repellant, a sunscreen, an emollient, etc.), the cosmetic stick composition according to the present invention can be a deodorant stick composition, an insect repellant stick, a sunscreen stick, a skin care stick, etc.

It has been desired to provide a soap-gelled, clear cosmetic stick composition, such as a soap-gelled, clear deodorant solid stick composition, which retains clarity over an extended period of time so as to have a long shelf life. Such clear stick compositions have widespread consumer appeal. It has been desired to provide such clear stick composition which maintains clarity for extended periods of time, e.g., prior to being purchased by the consumer and until the product has been used up by the consumer. In particular, it has been desired to provide such a clear stick composition, having a long shelf life, which avoids crystals forming in the stick.

It has also been desired to provide a soap-gelled clear cosmetic stick composition, such as a deodorant solid stick composition, having improved pliability while maintaining satisfactory rigidity of the stick. By improved pliability, we mean that the fracture potential of the cosmetic stick is reduced. Consequently, the consumer is better able to roll the stick product out of the dispensing package without the stick product fracturing, or to remove the cap from the dispensing package without breakage of the stick product. Improved pliability would reduce propensity of product breakage when the dispensing package cap is removed, where the product is stored with the end of the stick protruding from the dispensing package.

U.S. Pat. No. 4,759,924 to Luebbe, et al, the contents of which are incorporated herein by reference in their entirety, discloses transparent, soap-gelled cosmetic stick compositions containing a polyhydric aliphatic alcohol having 2–6 carbon atoms and 2–6 hydroxyl groups; water; a soap gel-forming agent; and a hydro-alcoholic soluble emollient having the formula $R(OC_3H_6)_a(OC_2H_4)_bOH$, where R is either hydrogen or a hydrocarbon chain having from about 1 to 18 carbon atoms, and $a/(a+b) \leq 0.5$. This patent discloses that the polyhydric alcohol can illustratively be ethylene glycol or propylene glycol, and that mixtures of polyols can be used; and that, illustratively, the soap gel-forming agent can be selected from the sodium, potassium and aluminum salts of saturated or unsaturated fatty acids containing from about 14 to 18 carbon atoms. Preferred soap gel-forming agents include sodium stearate, sodium palmitate, potassium stearate, potassium palmitate, sodium myristate and aluminum monostearate. Illustrative hydro-alcoholic soluble emollients include PPG-5-Ceteth 20, PPG-3-Myreth-3, PEG-20-laurate, PEG-6-32 and Polyoxamer 335.

U.S. Pat. No. 4,759,924 further discloses that the stick composition can include various optional ingredients, including conventional deodorant materials; and that the stick composition (gel stick) can be used by the consumer by rubbing the stick on the area of the body where application is desired. For example, in the case of a deodorant stick for underarm application, the stick is rubbed in the axillary area to apply the deodorant material.

While U.S. Pat. No. 4,759,924 describes a stick composition that is indicated as being transparent, this patent does not disclose maintenance of transparency, or clarity, of the stick over an extended period of time. Moreover, this patent is silent as to the pliability of the formed stick.

U.S. Pat. No. 5,128,123 to Brewster, et al, the contents of which are incorporated herein by reference in their entirety, discloses cosmetic compositions, in the form of sticks, which are clear and mild, containing (in addition to a polyhydric alcohol having from 2–6 carbon atoms and from 2–6 hydroxyl groups, water, and a soap gelling agent) both (a) an alkoxylate copolymer, and (b) a basic amine clarifying agent present in an effective amount to maintain clarity of the stick. The alkoxylate copolymer has a formula $[A-CH_2CH_2-A]_f[(C_2H_4O)_a(C_3H_6O)_b(C_2H_4O)_c(C_3H_6O)_d]_e[H]_g$, where A is nitrogen; a, b, c and d are independently selected integers ranging from 0 to 200 with the proviso that the sum of a, b, c and d is at least about 50; e is an integer from 1 to 4; f is an integer from 0 to 1; and g is an integer from 0 to 4. This patent discloses that the copolymer partially replaces soap as a structurant in the stick. This patent further discloses that when f and e are 0 and 1, respectively, the structure described is a poly(ethylene oxide) (propylene oxide) (ethylene oxide) copolymer. This patent further discloses that the clarifying agent is preferably selected from amino alkanols having from 2–6 hydroxyl groups, particularly effective being the propanol amines.

U.S. Pat. No. 5,128,123 also defines what is meant by the term "clear" with respect to the stick composition described therein. Specifically, the term "clear" has its usual dictionary definition; thus, a clear cosmetic stick, like glass, allows for ready viewing of objects behind it. This patent contrasts clear cosmetic sticks with translucent cosmetic sticks, which allow light to pass through but causes the light to be so scattered that it will be impossible to clearly identify objects behind the translucent stick. Thus, in the present art there is a difference between clear, translucent and opaque sticks. This patent goes on to define clear, translucent and opaque sticks based on transmittance of light of wavelengths in the range of 400 to 900 nm through a sample 1 cm thick.

While U.S. Pat. No. 5,128,123 discloses a clear cosmetic stick which is intended to maintain clarity over extended periods of time, this patent does not provide any disclosure concerning pliability of the product.

U.S. Pat. No. 4,822,602 to Sabatelli discloses a cosmetic stick composition including the following components: (a) water-soluble active; (b) dimethicone copolyol; (c) volatile silicone oil; (d) propylene glycol; (e) $C_2$–$C_4$ monohydric alcohol; (f) water; (g) solidifying agent; and (h) coupling agent. The "dimethicone copolyol" is defined in this patent as one or more polyalkylene oxide modified dimethylpolysiloxanes. The solidifying agent can vary depending upon the particular type of cosmetic stick desired (e.g., wax stick; gel stick), and can be a soap-type gel forming agent such as a sodium, potassium and/or aluminum salt of fatty acid containing from about 14 to about 18 carbon atoms.

U.S. Pat. No. 4,822,602 is not disclosed as being a clear cosmetic stick. Moreover, U.S. Pat. No. 4,822,602 is silent as to the pliability of the cosmetic stick produced.

Accordingly, it is still desired to provide a clear cosmetic stick composition, such as a clear deodorant stick composition, which is clear and maintains clarity over extended periods of time, and which provides a stick product having improved pliability while maintaining rigidity of the stick product.

SUMMARY OF THE INVENTION

Accordingly, it is an object of the present invention to provide a cosmetic stick composition (e.g., a deodorant solid stick composition) that is clear, with improved clarity, and which maintains such clarity over extended periods of time; in particular, over the shelf life and period of use of the stick composition by a consumer.

It is a further object of the present invention to provide a clear cosmetic stick composition, which is clear even when a cosmetically active material is incorporated therein, and which maintains clarity for relatively long periods of time (so as to have a relatively long shelf life as a clear product).

It is a further object of the present invention to provide a clear cosmetic stick composition, such as a clear deodorant stick composition, containing alcohol and water, and gelled by a soap (such as alkali metal salts of fatty acids), which maintains clarity for long periods of time, and wherein crystals do not form within the composition over these long periods of time.

It is a further object of the present invention to provide a cosmetic solid stick composition that is clear when having cosmetically active materials incorporated therein and that maintains such clarity, and that provides a stick product having improved pliability (to thereby reduce potential stick fracture as the stick is rolled out of a dispensing package or when the package cap is removed) while maintaining satisfactory stick product rigidity.

It is a further object of the present invention to provide a clear deodorant stick composition having deodorant active material incorporated therein, which can be applied, for example, to axillary regions of the body to reduce or avoid axillary malodor.

It is a still further object of the present invention to provide a clear deodorant stick composition, having deodorant active materials incorporated therein, that is clear and maintains clarity over extended periods of time, and has improved pliability while maintaining satisfactory rigidity.

The foregoing objects are achieved, according to the present invention, by incorporating, in the soap-gelled stick composition containing alcohol and water, at least one alkoxylate material selected from the group consisting of alkoxylate homopolymers and dimethicone copolyols, the alkoxylate material being included in the composition in an amount so as to provide a clarified (i.e., clear) composition. Illustratively, but not limiting, the alkoxylate material is included in the composition in an amount of 0.5–20% by weight, of the total weight of the composition.

Illustrative alkoxylate homopolymers include ethoxylate homopolymers and propoxylate homopolymers. The ethoxylate homopolymers include polyethylene glycols, as well as ethoxylated surface active agents (surfactants). These alkoxylate homopolymers according to the present invention differ from materials incorporated in the stick composition in U.S. Pat. No. 5,128,123 to Brewster, et al, which requires alkoxylate copolymers.

The foregoing objects are also achieved, according to the present invention, by incorporating non-ionic surfactants in the soap-gelled cosmetic stick composition containing alcohol and water. The non-ionic surfactant, illustratively, is incorporated in the composition in an amount of 0.5–20% by weight, of the total weight of the composition. Various alkoxylate homopolymers, including various ethoxylate homopolymers and various propoxylate homopolymers, are non-ionic surfactants that can be incorporated in the stick composition as clarifying agents according to the present invention.

Preferably, the soap gelling agent of the composition of the present invention contains salts of saturated or unsaturated fatty acids having carbon chain length $C_{12}$–$C_{22}$, with at least some of these salts being salts of fatty acids having carbon chain length of $C_{20}$ and/or $C_{22}$. Utilizing, e.g., sodium salts of long-chain saturated fatty acids of carbon chain length of $C_{20}$ and/or $C_{22}$ provides a product having a higher gelling temperature and improved stability.

However, a problem arises in utilizing such soap gelling agent that includes salts of fatty acids having carbon chain lengths of $C_{20}$ and/or $C_{22}$, in that there is increased crystallization in the stick composition over extended periods of time, disadvantageously affecting the clarity of the stick composition. Such crystallization can be reduced when incorporating the alkoxylate materials in the stick composition, according to the present invention.

The clear stick composition according to the present invention can include various active materials, including sunscreens, deodorant active materials, insect repellents, etc. As would be appreciated, depending on the active material incorporated, the product formed would be a sun protection stick, deodorant stick, insect repellant stick, etc. As for various active materials which can be incorporated in the stick composition according to the present invention, and amounts of these materials, see U.S. Pat. No. 5,128,123, the contents of which have previously been incorporated herein by reference in their entirety.

It is desirable not to include in the stick composition of the present invention components which would disadvantageously affect clarity of the final product. Accordingly, it is preferred that materials which reduce clarity are not incorporated in the composition of the present invention.

With the foregoing caveat, compositions according to the present invention can include various additional materials conventionally included in cosmetic stick compositions. Various materials incorporated in stick compositions are disclosed in U.S. Pat. No. 4,759,924 and U.S. Pat. No. 5,128,123, the contents of each of which have previously been incorporated herein by reference in their entirety. The additional materials can include, illustratively (and not limiting), polyols, fatty alcohols, alkanolamide, color (dyes), essential oils, soluble inorganic salts of sodium and potassium, etc.

Accordingly, by the present invention, which incorporates various alkoxylate materials selected from alkoxylate homopolymers and dimethicone copolyols, or non-ionic surfactants, in the soap-gelled stick composition containing water and alcohol, a solid stick composition is achieved that is clear, with improved clarity, and maintains clarity over relatively long periods of time; and that has improved pliability while maintaining satisfactory product rigidity. Moreover, various cosmetic active ingredients, such as deodorant active materials, can be incorporated in the composition, so as to provide, for example, clear deodorant stick compositions that retain clarity over long periods of time, while having improved pliability and good product rigidity.

DETAILED DESCRIPTION OF THE INVENTION

While the present invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Thus, while the description is most specific with respect to clear deodorant stick compositions, the present invention is not limited to deodorant compositions, but includes within its scope various cosmetic products, depending on the cosmetically active material incorporated in the stick composition.

Throughout the present disclosure, where compositions are described as including or comprising specific components or materials, it is contemplated by the inventors that compositions of the present invention also consist essentially of, or consist of, the recited components or materials. Accordingly, throughout the present disclosure any described composition of the present invention can consist essentially of, or consist of, the recited components or materials.

Throughout the present disclosure, various of the components of the disclosed compositions are denoted by their name in the *CTFA International Cosmetic Ingredient Dictionary* (4th Ed. 1991), the contents of which are incorporated herein by reference in their entirety.

The present invention is directed, in general, to clear cosmetic stick compositions. By clear, we mean the usual dictionary definition of this term. Thus, a clear cosmetic stick, like glass, allows for ready viewing of objects behind it. By contrast, a translucent cosmetic stick, although allowing light to pass through, causes the light to be so scattered that it will be impossible to clearly identify objects behind the translucent stick. Opaque sticks do not permit light to pass therethrough. Thus, according to the present invention there is a distinction between, e.g., "clear" and "translucent" cosmetic sticks.

Generally, a 1 cm slice of the stick composition according to the present invention will permit over a 60% transmittance of light of any wavelength in the range of 600–900 nm. However, we do not want to be limited to such 60% transmittance, relying on the usual dictionary definition of "clear" as discussed previously and known in the present art.

The present invention contemplates clear cosmetic stick compositions (for example, clear deodorant solid stick compositions) containing alcohol and water, and gelled with salts (soaps) of fatty acids (saturated or unsaturated fatty acids), the compositions further including alkoxylate materials selected from the group consisting of alkoxylate homopolymers and dimethicone copolyols, for clarifying the composition. The alkoxylate homopolymers are preferably those that act as non-ionic surfactants, more desirably those having a hydrophile-lipophile balance (HLB) of at least 24. The alkoxylate homopolymers which can be incorporated in the composition of the present invention are illustrated by the following compounds. These compounds illustrate the present invention, and are not limiting of the present invention. In the following, the CTFA adopted name is set forth, with a commercial product and vendor parenthetically set forth. Thus, these alkoxylated homopolymers include C14-15 Pareth-2.75 (Neodol 45-2.25, from Shell Chemical Co.); C14-15 Pareth-13 (Neodol 45-13, from Shell Chemical Co.); Ceteareth-55 (Plurafac A-39, from BASF Corp.); PPG-10 Cetyl Ether (Procetyl 10, from Croda, Inc.); PPG-50 Cetyl Ether (Procetyl 50, from Croda, Inc.); and PEG-6 Lauramide (Amidox L-5, from Stepan Co.).

Dimethicone copolyols can be utilized as the clarifying agent in the present invention. The dimethicone copolyol can have both ethylene oxide and propylene oxide side chains, or the polyalkylene oxide side chains can consist only of polyethylene oxide side chains or can consist only of polypropylene oxide side chains. Illustrative dimethicone copolyols include Abil B8851 and Abil B8852, which respectively is a dimethicone copolyol having only polyethylene oxide side chains and having only polypropylene oxide side chains; each of these dimethicone copolyols is a commercial product from Goldschmidt Chemical Corp.

In general, the alkoxylate materials according to the present invention will include at least 2 moles (more desirably, at least 2.25 moles) of the alkylene oxide (for example, ethylene oxide and/or propylene oxide) functionalities, to provide desired clarifying of the composition.

In the following is set forth various structural formulae for the alkoxylate materials according to the present invention. Materials falling within these structural formulae are illustrative materials which can be incorporated as part of the compositions of the present invention, and are not limiting.

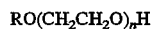        I $R=C_9-C_{18}$ hydrocarbon chain length
$n=2$ to $50$

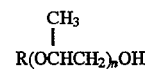        II $R=C_{12}-C_{18}$ hydrocarbon chain length
$n=2$ to $50$

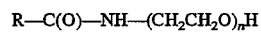        III $R=C_{12}-C_{18}$ hydrocarbon chain length
$n=2$ to $50$

An illustrative formula for the dimethicone copolyol is set forth in the following. Similarly, this formula is illustrative, and is not limiting of the present invention.

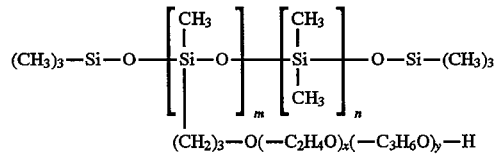        IV $m+n=10-30$ $x+y=100\%$.

By $x+y=100\%$, we mean that the total number of ethoxylate groups and propoxylate groups equals 100%; for example, the dimethicone copolyol can be 75% ethoxylated and 25% propoxylated.

The alcohol included in the solid stick composition of the present invention can be a monohydric and/or polyhydric alcohol (for example, ethanol as a monohydric alcohol, and propylene glycol and/or dipropylene glycol as polyhydric alcohols). The alcohol can be a mixture of alcohols, including a mixture of monohydric and polyhydric alcohols, or a mixture of monohydric alcohols or a mixture of polyhydric alcohols. Various polyhydric alcohols which can be used in soap-gelled alcohol- and water-containing stick compositions are described in U.S. Pat. No. 4,759,924, the contents of which have previously been incorporated herein by reference in their entirety, and can also be used in the present invention.

A necessary component of the cosmetic stick composition according to the present invention is a soap gel-forming agent. Sodium salts of fatty acids of carbon chain length $C_{12}$–$C_{22}$, e.g., sodium salts of saturated fatty acids having the above-mentioned carbon chain length, can be utilized as the gel-forming agent. Preferred gel-forming agents according to the present invention include sodium salts (that is, soaps) of relatively long-length-carbon-chain saturated fatty acids (for example, sodium salts of saturated fatty acids having carbon chain lengths of $C_{20}$ and/or $C_{22}$). The fatty acid portions of the soap can include a mixture of different saturated fatty acids of carbon chain length in the range $C_{12}$–$C_{22}$, preferably including some $C_{20}$ and/or $C_{22}$. By utilizing such relatively long-chain-length fatty acids, a product is provided having a relatively high melting temperature, and, correspondingly, relatively greater stability.

Preferred gel-forming agents according to the present invention include mixtures of sodium fatty acid soaps, having different fatty acid portions. For example, the soap gel-forming agent can be a mixture of sodium laurate, sodium myristate, sodium palmitate, sodium stearate, sodium arachidate, and sodium behenate, with the sodium fatty acid soaps respectively preferably having the following distribution:

| FATTY ACID DISTRIBUTION | |
|---|---|
| Fatty Acid Soap | % (By Weight, of the Soap Mixture) |
| Sodium laurate | 2% |
| Sodium myristate | 4–7% |
| Sodium palmitate | 35–44% |
| Sodium stearate | 31–44% |
| Sodium arachidate | 7–9% |
| Sodium behenate | 8–10% |

This mixture of sodium fatty acid soaps, having the desired distribution, can be provided in any number of ways known in the art. For example, pure sodium laurate, pure sodium myristate, etc., can be mixed together in desired proportions. Or different mixtures of sodium fatty acid soaps (for example, commercial grade sodium stearate, containing sodium stearate, sodium palmitate, etc., and another mixture of sodium fatty acid soaps) can be combined to provide the desired distribution.

The foregoing fatty acid soap distribution of the soap gel-forming agent is illustrative, and not limiting of the present invention.

Illustratively, and not limiting, the cosmetic stick composition according to the present invention can include the following amounts (in percent by weight, of the total weight of the composition) of other components than the alkoxylate material:

Alcohol (e.g., propylene glycol): 55–80 %
Water: 9–25%
Soap: 4–10%

Other materials can be included in the clear stick compositions according to the present invention, and include various cosmetically active materials. For example, and not limiting, stick compositions according to the present invention can include cosmetically active materials such as deodorant active materials (including fragrances and antibacterial agents), sunscreens, skin conditioners, nail conditioners and the like. For purposes of the present invention, these other materials should not unsatisfactorily affect clarity, and, where appropriate, should be able to be safely applied to the human body.

As indicated previously, compositions according to the present invention have use as underarm deodorant compositions (e.g., by application to axillary regions of the human body), when having deodorant active materials incorporated in the composition. Various deodorant active materials which can be included in the compositions according to the present invention, and amounts of these materials, are described in U.S. Pat. No. 4,759,924, the contents of which have previously been incorporated herein by reference in their entirety, and include (but are not limited to) fragrances (e.g., perfumes) and antibacterial agents (e.g., bacteriostats and bactericides), among others. For example, a deodorant active material useful as an antibacterial agent in the present invention is 2-4-4'-trichloro-2'-hydroxydiphenyl ether (CTFA name: Triclosan). An antibacterial agent such as Triclosan is not a required component of the composition, even where the composition is a deodorant stick composition to be applied to the axillary regions to combat body malodor.

Other ingredients such as dyes, pigments, coloring agents, etc., which do not disadvantageously affect the clarity of the solid stick compositions of the present invention, can desirably be incorporated in the soap-gelled compositions of the present invention, in amounts as conventionally incorporated and as discussed in U.S. Pat. No. 4,759,924.

The compositions according to the present invention are manufactured by processing techniques conventional in the art. Specifically, the solid components of the composition are melted and these melted components are mixed. Preferably, the fragrance (if any) is added close to the end of the manufacturing process (for example, is the last component added), with the previously mixed components being cooled to a lower temperature (while still maintaining a melt) prior to adding the fragrance, so as to limit any volatilization of the fragrance. While still in the liquid state, the composition is filled in a dispensing package (as conventional in the art) and then cooled to solidify the product in the package.

The compositions according to the present invention are utilized by conventional techniques. For example, when utilizing compositions according to the present invention as an axillary deodorant solid stick, having deodorant active materials (such as Triclosan and/or a fragrance) incorporated therein, the solid stick product is elevated out of the dispensing package so as to expose the end of the stick product, and the exposed portion of the stick product is then rubbed against, e.g., the axillary region of the human body so as to deposit the deodorant active materials on the skin in the axillary region.

While in the foregoing, the present invention has been described in terms of a deodorant solid stick composition for use in axillary regions, the present invention is not so limited; and the cosmetic stick composition according to the present invention has various uses depending on the active material incorporated therein, including (but not limited to) as a deodorant for other parts of the body, sun protection stick, insect repellant, skin softener, etc.

In the following, specific examples of compositions within the scope of the present invention will be set forth. Of course, these specific examples are illustrative of the present invention and are not limiting.

In the following examples, the stated percentages are percentages by weight, of the stated component, relative to the total weight of the composition. The names utilized are the CTFA names for the ingredients, where applicable.

In the following examples, soap gel-forming agent A is referred to. This soap gel-forming agent is a mixture of different sodium fatty acid soaps, with different fatty acid portions, as set forth in the following:

| Fatty Acid Soap | % (By Weight of the Soap Mixture) |
| --- | --- |
| Sodium laurate | 1 |
| Sodium myristate | 4–10 |
| Sodium palmitate | 20–30 |
| Sodium stearate | 25–42 |
| Sodium arachidate | 15–18 |
| Sodium behenate | 17–20 |

| Ingredients | |
| --- | --- |
| EXAMPLE I | |
| Soap Gel-Forming Agent A | 6 |
| Propylene Glycol | 79 |
| Water | 13 |
| PPG-50 Cetyl Ether (Procetyl 50) | 2 |
| EXAMPLE II | |
| Soap Gel-Forming Agent A | 6 |
| Propylene Glycol | 79 |
| Water | 13 |
| PPG-10 Cetyl Ether (Procetyl 10) | 2 |
| EXAMPLE III | |
| Soap-Gel Forming Agent A | 6 |
| Propylene Glycol | 77 |
| Water | 11 |
| Ceteareth 55 (Plurafac A-39) | 6 |
| EXAMPLE IV | |
| Soap Gel-Forming Agent A | 6 |
| Propylene Glycol | 75 |
| Water | 13 |
| Dimethicone Copolyol (Abil B 8551) | 6 |
| EXAMPLE V | |
| Soap Gel-Forming Agent A | 6 |
| Propylene Glycol | 77 |
| Water | 11 |
| Dimethicone Copolyol (Abil B 8552) | 6 |
| EXAMPLE VI | |
| Soap Gel-Forming Agent A | 6 |
| Propylene Glycol | 77 |
| Water | 11 |
| C 14–15 Pareth-2.25 (Neodol 45-2.25) | 6 |
| EXAMPLE VII | |
| Soap Gel-Forming Agent A | 6 |
| Propylene Glycol | 77 |
| Water | 11 |
| C 14–15 Pareth-13 (Neodol 45-13) | 6 |

Accordingly, by including the alkoxylate material as part of a soap-gelled cosmetic stick composition containing alcohol and water, and gelled with a soap gelling agent, according to the present invention, a clear cosmetic stick composition with improved clarity, which maintains improved clarity over extended periods of time, is achieved. Moreover, such stick composition has improved pliability while maintaining good rigidity. Furthermore, various cosmetically active materials, including deodorant active materials, such as conventional deodorant active materials, can be incorporated in the stick composition, so as to provide, e.g., a deodorant stick, while maintaining the aforementioned good properties (including clarity, rigidity and pliability).

Attention is directed to the concurrently filed U.S. patent application of Makarand Shevade, Bhalchandra D. Moghe and Radhakrishna B. Kasat "Clear Cosmetic Stick Composition Containing a Combination of Anionic and Non-Ionic Surfactants" (Attorney Docket No. 851.33536X00), U.S. patent application Ser. No. 08/448,104, filed May 23, 1995, the contents of which are incorporated herein by reference in their entirety.

While we have shown and described several embodiments in accordance with the present invention, it is understood that the same is not limited thereto, but is susceptible of numerous changes and modifications as known to those skilled in the art. Therefore, we do not wish to be limited to the details shown and described herein, but intend to cover all such changes and modifications as are encompassed by the scope of the appended claims.

We claim:

1. A clear cosmetic stick composition comprising alcohol and water, and gelled with a soap gelling agent constituted by salts of fatty acids, the composition further including at least one alkoxylate material selected from the group consisting of dimethicone copolyols, for clarifying the composition, the at least one alkoxylate material being included in the composition in an amount so as to clarify the composition.

2. A clear cosmetic stick composition according to claim 1, wherein the composition includes 0.5–20% by weight, of the total weight of the composition, of the at least one alkoxylate material.

3. A clear cosmetic stick composition according to claim 1, wherein the soap gelling agent is a mixture of salts of fatty acids having a carbon chain length within the range of $C_{12}$–$C_{22}$.

4. A clear cosmetic stick composition according to claim 3, wherein the soap gelling agent includes salts of fatty acids having a carbon chain length of at least one of $C_{20}$ and $C_{22}$.

5. A clear cosmetic stick composition according to claim 4, wherein the composition further includes a deodorant effective amount of a deodorant active material, whereby a clear deodorant stick composition, to combat body malodor, is provided.

6. A clear cosmetic stick composition according to claim 5, wherein the deodorant active material is selected from the group consisting of fragrances and antibacterial agents.

7. A clear cosmetic stick composition according to claim 1, wherein the composition further includes a deodorant effective amount of a deodorant active material, whereby a clear deodorant stick composition, to combat body malodor, is provided.

8. A clear cosmetic stick composition according to claim 1, wherein the dimethicone copolyols have a formula:

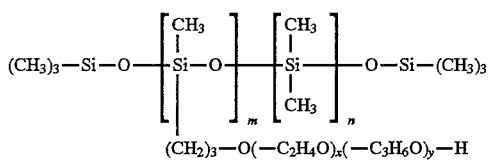

where m+n is from 10 to 30, m and n each being integers greater than 0, and x+y=100%.

9. A clear cosmetic stick composition according to claim 8, wherein the composition includes, in percent by weight of the total weight of the composition, 55–80% alcohol, 9–25% water and 4–10% soap gelling agent.

10. A clear cosmetic stick composition according to claim 9, wherein the composition includes 0.5–20% by weight, of the total weight of the composition, of the at least one alkoxylate material.

11. A clear cosmetic stick composition according to claim 10, wherein the soap gelling agent includes salts of fatty acids having a carbon chain length within the range of $C_{12}$–$C_{22}$.

12. A clear cosmetic stick composition according to claim 11, wherein the soap gelling agent includes salts of fatty acids having a carbon chain length of at least one of $C_{20}$ and $C_{22}$.

13. A clear cosmetic stick composition according to claim 11, wherein the composition further includes a deodorant effective amount of a deodorant active material, whereby a clear deodorant stick composition, to combat body malodor, is provided.

14. A clear cosmetic stick composition according to claim 13, wherein the deodorant active material is selected from the group consisting of fragrances and antibacterial agents.

15. A clear cosmetic stick composition according to claim 1, wherein polyalkylene oxide side chains of the at least one dimethicone copolyol consist of polyethylene oxide side chains.

16. A clear cosmetic stick composition according to claim 1, wherein polyalkylene oxide side chains of the at least one dimethicone copolyol consist of polypropylene oxide side chains.

17. A clear cosmetic stick composition according to claim 1, wherein the hydrophile-lipophile balance of the at least one alkoxylate material is at least 24.

18. A clear cosmetic stick composition, comprising, in percent by weight of the total weight of the composition:

(a) 55–80% by weight, propylene glycol;

(b) 9–25% by weight water;

(c) 4–10% by weight sodium stearate gelling agent; and (d) 0.5–20% by weight of an alkoxylate material selected from the group consisting of dimethicone copolyols.

19. A clear cosmetic stick composition according to claim 18, further including a deodorant active material in a deodorant effective amount, so as to provide a clear deodorant stick composition.

20. A clear cosmetic stick composition according to claim 19, wherein the deodorant active material is at least one selected from the group consisting of fragrances and antibacterial agents.

21. A method of reducing body malodor, comprising rubbing the clear deodorant stick composition of claim 5 on axillary regions of the human body.

22. A method of reducing body malodor, comprising rubbing the clear deodorant stick composition of claim 13 on axillary regions of the human body.

23. A method of reducing body malodor, comprising rubbing the clear deodorant stick composition of claim 19 on axillary regions of the human body.

* * * * *